(12) United States Patent
Raja et al.

(10) Patent No.: US 8,779,124 B2
(45) Date of Patent: *Jul. 15, 2014

(54) AMMOXIMATION PROCESS

(71) Applicant: University of Southampton, Southampton (GB)

(72) Inventors: Robert Raja, Eastleigh (GB); Alexander James Patterson, Coupar Angus (GB)

(73) Assignee: University of Southampton, Southampton (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/889,404

(22) Filed: May 8, 2013

(65) Prior Publication Data
US 2013/0245322 A1  Sep. 19, 2013

Related U.S. Application Data

(63) Continuation of application No. 13/139,930, filed as application No. PCT/GB2010/000010 on Jan. 6, 2010, now Pat. No. 8,444,917.

(30) Foreign Application Priority Data

Jan. 7, 2009  (GB) .................................. 0900198.3

(51) Int. Cl.
C07C 249/04 (2006.01)
C07C 251/32 (2006.01)
C07D 201/04 (2006.01)

(52) U.S. Cl.
USPC ............................ 540/535; 540/536; 564/267

(58) Field of Classification Search
USPC .................... 564/267; 540/535, 536
See application file for complete search history.

(56) References Cited

U.S. PATENT DOCUMENTS

| | | | |
|---|---|---|---|
| 4,801,364 A | 1/1989 | Wilson | |
| 4,894,478 A | 1/1990 | Roffia et al. | |
| 4,917,876 A | 4/1990 | Lok et al. | |
| 4,956,165 A | 9/1990 | Lok et al. | |

FOREIGN PATENT DOCUMENTS

| EP | 1674449 A1 | 6/2006 |
|---|---|---|
| GB | 2450711 A | 1/2009 |
| WO | 2004/052237 A1 | 6/2004 |
| WO | 2009/004342 A1 | 1/2009 |

OTHER PUBLICATIONS

Thomas, John Meurig et. al., "Design of a "green" one-step catalytic production of ε-caprolactum (precursor of nylon-6)", Proceedings of the National Academy of Sciences of the United States of America, 102(39), 13732-13736 CODEN: PNASA6; p. 13733, col. 2—p. 13735; table 2.

Raja, R. et al., "Bifunctional Molecular Sieve Catalysts for the benign ammoximation of cyclohexanone: one-step, solvent-free production of oxime and ε-caprolactam with a mixture of air and ammonia", Journal of the American Chemical Society, New York, USA, vol. 123, Jan. 1, 2001, pp. 8153, col. 2, line 4—line 29—8154; table 1.

Jihong, Yu et al., "Rich structure chemistry in the aluminophosphate family", Accounts of Chemical Research, ACS, Washington DC, US, vol. 36, No. 7, Jan. 1, 2003, pp. 481-490.

Thomas, John Meurig et al., "Catalytically active centres in pourous oxides; design and performance of highly selective new catalysts", Chem Comm., 2001, pp. 675-687.

Zhou, Lipeng et al., "Synthesis of FeCoMnAPO-5 molecular sieve and catalytic activity in cyclohexane oxidation by oxygen", Catalysis Letter, vol. 99, No. 3-4, p. 231-234 (2005).

M.W. Goldblatt et al., "ε-Caprolactam", Brit. J. industr. Med., 1954, 11,1.

International Search Report mailed Apr. 4, 2010.

John Meurig Thomas et al., Design of a "green" one-step catalytic production of E-caprolactam (precursor of nylon-6), PNAS, pp. 13732-13736, No. 39, vol. 102, dated Sep. 27, 2005.

Japanese Patent Application No. 2010-514122, Notification of Reasons for Rejection, dated Feb. 21, 2013.

Chinese Patent Application No. 201080003411.6, First Office Action, dated Dec. 3, 2013.

*Primary Examiner* — Bruck Kifle
(74) *Attorney, Agent, or Firm* — Banner & Witcoff, Ltd.

(57) ABSTRACT

A redox ammoximation process in which a ketone or aldehyde is reacted with ammonia and oxygen in the presence of a catalyst, wherein: the catalyst is an aluminophosphate based redox catalyst having the qualitative general formula (I) $M^1M^2AlPO-5$ (I) in which $M^1$ is at least one transition metal atom having redox catalytic capability; $M^2$ is at least one metal atom in the (IV) oxidation state; $M^1$ and $M^2$ are different from each other; and a proportion of the phosphorous atoms in the $M^1M^2AlPO-5$ type structure are replaced by $M^2$ atoms.

14 Claims, 3 Drawing Sheets

AMMOXIMATION PROCESS

The present invention relates to an ammoximation process using a redox catalyst comprising an aluminophosphate, commonly referred to as an "AlPO" system.

AlPO compounds are well known and are known for use as molecular sieves and as catalysts for various processes, for example as described in U.S. Pat. No. 4,567,029. They are nanoporous solids with channels permeating the whole of the material, thus giving the material a very substantial surface area, which can be used for catalysis. The basic structure comprises aluminium, phosphorous and oxygen atoms, in which some of the aluminium atoms have been replaced by one or more other atoms, to provide the required catalytic activity.

J. M. Thomas & R. Raja, [*Design of a "green" one-step catalytic production of ϵ-caprolactam (precursor of nylon-6)*, Proceedings Natl. Acad. Sci. USA, 102, 13732-13736 (2005)]; R. Raja, G. Sankar & J. M. Thomas, [*Bifunctional molecular sieve catalysts for the benign ammoximation of cyclohexanone: One-step, solvent-free production of oxime and ϵ-caprolactam with a mixture of air and ammonia*, J. Am. Chem. Soc. 123, 8153-8154 (2001)]; and Nature (October 2005, Vol. 437; page 1243) describe a process for preparing certain precursors to nylon, especially s-caprolactam, using such AlPO catalysts, specifically AlPO catalysts having at least two active sites, one being a redox site, generally based upon Co(III), Mn(III) or Fe(III) atoms, and the other being a Brønsted acid site, generally based on Zn(II), Mg(II) or Co(II) atoms. In these structures both metals replace aluminium in the ALPO structure. The two types of site are well separated in the three dimensional AlPO structure and operate separately on the feedstock. As a result, it is possible to convert the cyclohexanone feedstock into ϵ-caprolactam with an efficiency in excess of 70%, up to around 80%, in a single step, rather than use the multi-step procedure currently used—see Nature (op cit).

However, for commercial purposes, a 70% conversion is inadequate, and so, although the reaction proposed in the above literature is very elegant and of considerable scientific interest, it is presently of little commercial value.

Furthermore, there is a desire to produce compounds which can act as intermediates for other useful products. These intermediates include oximes, especially cyclohexanone-oximes.

As disclosed in International patent application no. PCT/GB2008/002286 the present inventors surprisingly found that a modification of the catalyst used in the reaction described above is capable of carrying out ammoximation with a better yield. The resulting oxime may then be converted efficiently, using well known reactions, to the desired ϵ-caprolactam.

In particular, International patent application no. PCT/GB2008/002286 discloses a redox ammoximation process in which a ketone or aldehyde is reacted with ammonia and oxygen in the presence of a catalyst, where the catalyst is an aluminophosphate based redox catalyst having at least two different redox catalytic sites comprising different transition metal atoms. The catalyst disclosed in International patent application no PCT/GB2008/002286 has the qualitative general formula (I) or (II):

or

in which $M^1$ and $M^2$ are different from each other and each represents a transition metal atom having redox catalytic capability; and some of the phosphorus atoms may be replaced by other equivalent atoms.

Although the catalysts disclosed in International patent application no PCT/GB2008/002286 provided improved catalytic properties over known catalysts in, for example, carrying out ammoximation reactions, the present inventors have prepared novel catalysts which surprisingly show improved catalytic properties or comparative catalytic properties over those disclosed in International patent application no PCT/GB2008/002286. The catalysts disclosed herein show high selectivity and conversion rates (mol %) for cyclohexane oxime when the ammoximation of cyclohexanone with ammonia is carried out using air as an oxidant.

It is an object of the present invention to address at least some of the problems and disadvantages of the prior art and to provide an efficient and selective ammoximation process.

In the first aspect of the present invention there is provided a redox ammoximation process in which a ketone or aldehyde is reacted with ammonia and oxygen in the presence of a catalyst, wherein:

the catalyst is an aluminophosphate based redox catalyst having the qualitative general formula (I)

in which $M^1$ is at least one transition metal atom having redox catalytic capability;

$M^2$ is at least one metal in the (IV) oxidation state;

$M^1$ and $M^2$ are different from each other; and a proportion of the phosphorous atoms in the $M^1M^2$AlPO-5 type structure are replaced by $M^2$ atoms.

In the second aspect of the present invention there is provided an aluminophosphate based redox catalyst having the qualitative general formula (I)

in which $M^1$ is at least one transition metal atom having redox catalytic capability;

$M^2$ is at least one metal in the (IV) oxidation state;

$M^1$ and $M^2$ are different from each other; and a proportion of the phosphorous atoms in the $M^1M^2$AlPO-5 type structure are replaced by $M^2$ atoms.

The term "the aluminophosphate having the qualitative general formula (I): $M^1M^2$AlPO (I)" as used herein is used to describe a bimetallic-substituted aluminophosphate molecular sieve catalyst. Aluminophosphates are made up of alternating $AlO_4^{5-}$ and $PO_4^{3-}$ tetrahedral linked together by a common oxygen bridge. These unites combine together to produce a variety of secondary building units which join together in different arrangements to form the AlPO-5 structure. The redox and active sites are generated by the replacement (isomorphorous substitution) of small amounts of the framework aluminium and phosphate with $M^1$ and $M^2$ ions. This is exemplified diagrammatically in FIG. 1. By performing only minimal isomorphorous substitution (typically from about 2% to 18%, or from about 2 to 10% by weight of the aluminium ions and from about 2% to 18%, or from about 2 to 10% by weight of the phosphorus ions) two types of active site are generated which are typically well separated (and typically isolated) and usually substantially uniformly distributed throughout the AlPO framework, thus generating two coexisting, single-site heterogenous catalysts. Metal containing aluminophosphates and processes for their preparation are known in the art, details of which are given below. The terminology "$M^1M^2$AlPO" is well known in the art, see for example, R. Raja, G. Sankar & J. M. Thomas, [*Bifunctional molecular sieve catalysts for the benign ammoximation of cyclohexanone: One-step, solvent-free production of oxime and ε-caprolactam with a mixture of air and ammonia*, J. Am. Chem. Soc. 123, 8153-8154 (2001)].

The term "$M^1M^2AlPO$-5" type structure is used to describe open-framework of the aluminophosphate molecular sieves. Such structures are well known in the art.

The term "wherein a proportion of the phosphorous atoms in the $M^1M^2AlPO$-5 type structure are replaced by $M^2$ atoms"; is used to describe wherein a proportion of the phosphorus atoms in Formula (I) are replaced by $M^2$ atoms which results in isomorphorous substitution into the AlPO framework. For example, some of the phosphorous atoms may be replaced by titanium atoms. Typically from 2 to 18% by weight, more preferably from 2 to 10% by weight of phosphorous ions will be replaced by $M^2$ ions.

A metal atom with redox capability is defined herein as one in which there is a change in the oxidation state of the metal atom during the catalytic process. For example, Co(III), Mn(III), etc are reduced to Co(II) and Mn(II) during the catalytic process. Without being bound to any particular theory, it is thought that the change in oxidation state leads to the formation of free-radicals (initiation step) which leads to the concomitant oxidation of the ketone to the oxime via a free-radical pathway in the presence of oxygen.

Each aspect as defined herein may be combined with any other aspect or aspects unless clearly indicated to the contrary. In particular any feature indicated as being preferred or advantageous may be combined with any other feature or features indicated as being preferred or advantageous.

Without wishing to be bound by any particular theory, it is believed that the incorporation of $M^2$ centres (preferably Ti(IV)) in conjunction with a redox site ($M^1$) (in particular Co(III) and Mn(III)) results in the generation of tetrahedral $M^2$ (preferably Ti(IV)) active sites. This has been evidenced by Diffuse Reflectance UV/Vis studies. In contrast to this in monometallic TiAlPO-5 catalysts, a distinctive peak broadening is observed at 230 nm. This is thought to be due to the presence of octahedral titanium species. It appears that the presence of the tetrahedral redox active centres of $M^1$ in close proximity to the tetrahedral $M^2$ (preferably Ti(IV)) has a synergistic influence of both the catalytic activity and the selectivity of the redox sites, resulting in an improved catalyst, and an improved ammoximation process.

$M^1$ is a transition metal atom having redox catalytic capability. Preferably $M^1$ is selected from Co(III), Mn(III), Fe(III), Cr(VI), Cu(III), V(V), Ru(III), and mixtures thereof. In one embodiment $M^1$ is selected from one of Co(III), Mn(III), Fe(III), Cr(VI), Cu(III), V(V) and Ru(III). More preferably $M^1$ is selected from Co(III), Mn(III), Fe(III) and mixtures thereof. More preferably still $M^1$ is selected from Co(III), Mn(III) and mixtures thereof.

$M^2$ is at least one metal in the (IV) oxidation state. Preferably, $M^2$ is selected from is at least one Ge(IV), Sn(IV), a transition metal in the (IV) oxidation state and mixtures thereof. For example, $M^2$ may be at least one transition metal in the (IV) oxidation state selected from Ti(IV), Re (IV), V(IV) and mixtures thereof. Preferably, $M^2$ is selected from Ge(IV), Sn(IV), Ti(IV), Re (IV), V(IV) and mixtures thereof. In one embodiment $M^2$ is selected from one of Ge(IV), Sn(IV), Ti(IV), Re (IV), and V(IV). In another embodiment In one embodiment $M^2$ is selected from one of Ge(IV), Sn(IV), Re (IV), V(IV) and mixtures thereof. More preferably, $M^2$ is selected from Ti(IV), V(IV) and mixtures thereof. More preferably still, $M^2$ is Ti(IV).

In one embodiment $M^2$ is at least one transition metal in the (IV) oxidation state other than Ti(IV).

In another embodiment $M^1$ is selected from Co(III), Mn(III), Fe(III), Cr(VI), Cu(III), V(V), Ru(III), and mixtures thereof, and $M^2$ is selected from at least one of Ge(IV), Sn(IV), transition metal in the (IV) oxidation state and mixtures thereof. Preferably $M^1$ is selected from Co(III), Mn(III), Fe(III) and mixtures thereof and $M^2$ is selected from one of Ge(IV), Sn(IV), Ti(IV), Re (IV), V(IV) and mixtures thereof.

In another embodiment $M^1$ is selected from Co(III), Mn(III), Fe(III), Cr(VI), Cu(III), V(V), Ru(III), and mixtures thereof, and $M^2$ is selected from at least one transition metal in the (IV) oxidation state and mixtures thereof. Preferably $M^1$ is selected from Co(III), Mn(III), Fe(III) and mixtures thereof and $M^2$ is selected from at least one of Ti(IV), Re (IV), V(IV) and mixtures thereof.

In a further embodiment $M^1$ is selected from Co(III), Mn(III), Fe(III), Cr(VI), Cu(III), V(V), Ru(III), and mixtures thereof, and $M^2$ is selected from Ge(IV), Sn(IV) and mixtures thereof. Preferably $M^1$ is selected from Co(III), Mn(III), Fe(III) and mixtures thereof and $M^2$ is selected from Ge(IV), Sn(IV) and mixtures thereof.

In a preferred embodiment, the catalyst is selected from $Co^{III}Ti^{IV}AlPO$, $Mn^{III}Ti^{IV}AlPO$, $Fe^{III}Ti^{IV}AlPO$, $Cr^{VI}Ti^{IV}AlPO$, $Cu^{III}Ti^{IV}AlPO$, $V^{V}Ti^{IV}AlPO$ and $Ru^{III}Ti^{IV}AlPO$. More preferably the catalyst is selected from $Co^{III}Ti^{IV}AlPO$ and $Mn^{III}Ti^{IV}AlPO$.

In one embodiment only one type of $M^1$ and one type of $M^2$ are present in the catalyst. In another embodiment at least two types of $M^1$ and one type of $M^2$ are present in the catalyst. In another embodiment at least one type of $M^1$ and two types of $M^2$ are present in the catalyst. In still another embodiment at least two types of $M^1$ and at least two types of $M^2$ are present in the catalyst.

Specifically preferred examples of these catalysts are $Co^{III}Ti^{IV}AlPO$-5 or $Mn^{III}Ti^{IV}AlPO$-5. These are of particular use in the ammoximation processes and specifically the use in the ammoximation of cyclohexanone.

The catalyst of the present invention may include silicon (IV). Preferably, Si(IV) replaces at least a proportion of the phosphorus atoms in the $M^1M^2AlPO$-5 type structure. Thus, in one embodiment of the present invention the aluminophosphate based redox catalyst has the qualitative general formula (II)

$$M^1M^2SiAlPO\text{-}5 \tag{II}$$

in which $M^1$ is at least one transition metal atom having redox catalytic capability;

$M^2$ is at least one metal in the (IV) oxidation state;

$M^1$ and $M^2$ are different from each other; and a proportion of the phosphorous atoms in the $M^1M^2AlPO$-5 type structure are replaced by $M^2$ atoms.

The references to $M^1$ and $M^2$ as described herein with reference to formula (I) apply equally to $M^1$ and $M^2$ in formula (II).

Metal containing aluminophosphate catalysts and processes for their preparation are known in the art. Catalysts containing a single redox catalyst site are described, for example, in U.S. Pat. No. 4,567,029, "Catalytically active centres in porous oxides: design and performance of highly selective new catalysts", J. M. Thomas and R. Raja, Chem. Comm., 2001, 675-687 and "Design of a green one-step catalytic production of ε-caprolactam (precursor of nylon-6)", J. M Thomas and R. Raja, PNAS, Vol 102/39), 13732-13736. The catalysts with two metal sites can be prepared in a similar manner. Catalysts with three metal sites can also be prepared in a similar manner, see for example, Catal. Lett. 99, 2005, 231 by Zhou et al.

In outline the procedure is as follows: the phosphorous source (typically 85% $H_3PO_4$) and the requisite amount of distilled deionised $H_2O$ are first mixed, for example gently stirred (400 rpm), for example using a mechanical stirrer in a Teflon-lined autoclave. To this the aluminium source (typically Al(OH)$_3$) is added, preferably slowly. The two redox metal sources ($M^1$ and $M^2$) are dissolved in water and then added, preferably slowly, to the previously prepared Al—$H_3PO_4$ mixture (preferably under stirring). An appropriate (depending on the desired structure-type) template (structure-directing agent) is then introduced, drop wise, under vigorous stirring (e.g. at 1700 rpm) and the gel is aged, for example, for about 1-2 hours at 298 K. The gel is then heated in order to synthesize a desired structure-type, for example it may be sealed in the Teflon-lined stainless steel autoclave and heated to the desired temperature, under autogenous pressure, for the required amount of time. The solid product is isolated, preferably by filtration or centrifugation (after crystallization), washed with copious amounts of distilled deionised water and dried under vacuum (90-120° C.). The as-prepared product is calcined for example at 550° C., first in nitrogen for 4 hours and then in dry oxygen for 16 hours, before its use as a catalyst.

Phase purity, structural integrity and crystallinity of the final catalyst may be confirmed by using a combination of powder x-ray diffractometry (XRD), X-ray absorption spectroscopy (XAS) and high resolution electron tomography. The precise stoichiometry (with an error of ca$\pm 3 \times 10^{-3}$) may be determined by ICP (metal) analysis.

The present invention will now be described further, by way of example only, with reference to the following drawings, in which.

Figure 1:
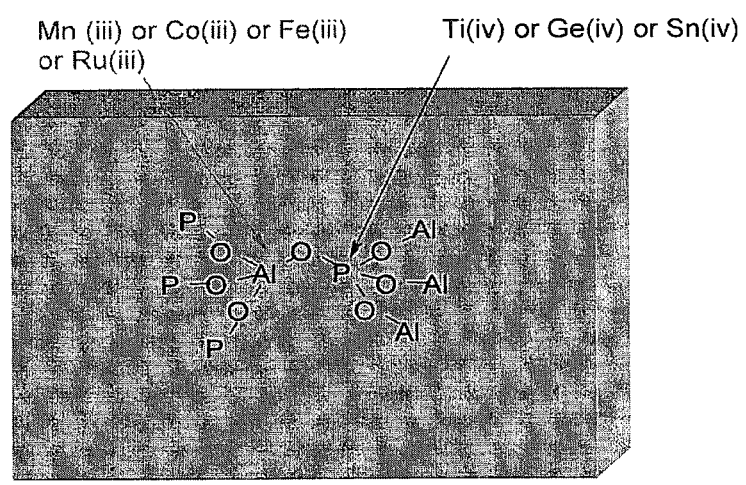
FIG. 1 is a schematic diagram of the substitution sites.

In the process of the present invention a ketone or aldehyde is reacted with ammonia and oxygen. The ketone or aldehyde may be any ketone or aldehyde, for example a $C_3$-$C_{20}$ ketone or $C_2$-$C_{20}$ aldehyde, and may be linear, branched or cyclic. Preferred ketones are cyclic ketones, for example $C_5$-$C_{12}$ cyclic ketones, with $C_6$ and $C_{12}$ ketones being the most preferred. Cyclohexanone is a particularly preferred ketone. Preferred aldehydes contain a cyclic or aromatic ring, especially a $C_6$ ring. A preferred aldehyde is benzaldehyde. The ketone or aldehyde may be unsubstituted or substituted, for example by a $C_1$-$C_4$ alkyl or alkenyl group, —OH or halogen. The ammonia may be in the form of a gas or dissolved in a solvent such as water. For commercial applications, preferably it will be in the form of a gas. In other applications, it may be preferable that it is in the form of aqueous ammonium hydroxide. Other than the water present from the aqueous ammonium hydroxide, no additional solvent is normally needed but it may be used if desired. If additional solvent is used, it is preferably inert. The oxygen is provided in the form of a gas, for example as $O_2$ or air.

The reaction product is generally an oxime corresponding to the ketone or aldehyde starting material. Thus, for example, the present invention can be used for the ammoximation of cyclohexanone to cyclohexanone-oxime, which is a precursor to ε-caprolactam, ε-caprolactam itself being an important precursor to nylon-6, for which there is a large and growing market, and so this reaction is particularly preferred. It can also be used for the ammoximation of benzaldehyde to benzaldehyde-oxime. In this reaction, cyclohexanone or benzaldehyde is reacted with ammonia (preferably in the gaseous form for commercial application, however it may be in the form of aqueous ammonium hydroxide) and oxygen (which may be provided in the form of pure oxygen or air) in the presence of the catalyst.

The reaction will take place over a wide range of temperatures and pressures, and the exact temperature and pressure chosen is not critical to the present invention. However, we generally prefer to carry out the reaction with heating, e.g. a temperature in the range from 40 to 200° C., preferably from 50 to 150° C., more preferably from 50 to 90° C. A pressure of, for example, from 0.5 MPa [5 bar] to 10 MPa [100 bar], is preferably used, more preferably 1 to 5 MPa and most preferably 3 [30 bar] to 3.5 MPa [35 bar].

The oxime produced may be converted into other compounds, for example a lactam. A suitable method is described in PNAS 102 (39) 13732-13736 using the Beckmann rearrangement.

The oxime may be converted to ε-caprolactam by known methods. One such known method is described in K Weissermel and H. J. Arpe, Industrial Organic Chemistry 1978, p 255.

The process of the present invention provides the oxime product in an unexpectedly high conversion rate and at good selectivity. The data in Table 1 of J. Am. Chem. Soc. 2001, 123, 8153-4 shows a conversion rate at 6 hours of up to 20%. The process of the present invention achieves a conversion rate of at least 40%, preferably at least 50%, or at least 60% as described in the following Examples.

In one aspect of the present invention there is provided an aluminophosphate based redox catalyst having the qualitative general formula (I)

$$M^1M^2AlPO\text{-}5 \qquad (I)$$

in which $M^1$ is at least one transition metal atom having redox catalytic capability;

$M^2$ is at least one metal in the (IV) oxidation state;

$M^1$ and $M^2$ are different from each other; and a proportion of the phosphorous atoms in the $M^1M^2AlPO$-5 type structure are replaced by $M^2$ atoms.

$M^1$ is at least one transition metal atom having redox catalytic capability. Preferably $M^1$ is selected from Co(III), Mn(III), Fe(III), Cr(VI), Cu(III), V(V), Ru(III), and mixtures thereof. In one embodiment $M^1$ is selected from one of Co(III), Mn(III), Fe(III), Cr(VI), Cu(III), V(V) and Ru(III). More preferably $M^1$ is selected from Co(III), Mn(III), Fe(III) and mixtures thereof. More preferably still $M^1$ is selected from Co(III), Mn(III) and mixtures thereof.

$M^2$ is at least one metal in the (IV) oxidation state. Preferably, $M^2$ is selected from at least one of Ge(IV), Sn(IV), a transition metal in the (IV) oxidation state and mixtures thereof. For example, $M^2$ may be at least one transition metal in the (IV) oxidation state selected from Ti(IV), Re (IV), V(IV) and mixtures thereof. Preferably, $M^2$ is selected from Ge(IV), Sn(IV), Ti(IV), Re (IV), V(IV) and mixtures thereof. In one embodiment $M^2$ is selected from one of Ge(IV), Sn(IV), Ti(IV), Re (IV), and V(IV). $M^2$ may be selected from Ge(IV), Sn(IV), Re (IV), V(IV) and mixtures thereof. More preferably, $M^2$ is selected from Ti(IV), V(IV) and mixtures thereof. More preferably still, $M^2$ is Ti(IV).

In a preferred embodiment, the catalyst is selected from $Co^{III}Ti^{IV}AlPO$, $Mn^{III}Ti^{IV}AlPO$, $Fe^{III}Ti^{IV}AlPO$, $Cr^{VI}Ti^{IV}AlPO$, $Cu^{III}Ti^{IV}AlPO$, $V^{V}Ti^{IV}AlPO$ and Ru$^{III}$Ti$^{IV}$AlPO. More preferably the catalyst is selected from Co$^{III}$Ti$^{IV}$AlPO and Mn$^{III}$Ti$^{IV}$AlPO.

The present invention will be further illustrated with reference to the following non-limiting Examples.

The AlPO-5 structures were synthesized using N-methyl-dicyclohexylamine (MDCHA) as the structure directing agent (SDA). The desired framework was achieved by starting with the correct gel composition for hydrothermal synthesis, i.e. the correct ratios of aluminium, phosphorous, metal, SDA and water. The general synthesis procedure is given below, with specific reaction conditions for each sample.

Experimental Procedure

Aluminium hydroxide (~0.053 mols) and phosphoric acid (0.098 mols) were combined in a PTFE beaker with 20 ml of water and left stirring for 20 minutes to obtain a homogeneous mixture. For bimetallic AlPOs, the two metal precursors were dissolved in two separate beakers and left stirring before being added dropwise simultaneously to the aluminium/phosphorus mixture. The resulting gel was left for 30 minutes to homogenize before the structure directing agent was added dropwise with the rest of the water, and left for 1 hour stirring vigorously. The gel was then divided into three Teflon lined autoclaves and crystallized at 140-200° C. for 2 hours (for AFI framework).

After crystallization, the sample was quenched and washed with water before calcination at 550° C. under a flow of air for 8 hours. The resulting sample was then stored under nitrogen to minimise the reduction of the metal sites in the AlPO framework, the specific reaction conditions are listed in Table 1.

TABLE 1

List of conditions for the phase pure sample synthesized

|  | MAlPO | Gel Composition | SDA[a] | Loading[b] (Atom %) | Time[c] (hours) | Temp[d] |
|---|---|---|---|---|---|---|
| Comparative Example | CoAlPO-5 | 0.96Al:1.5P:0.8R:40H$_2$O | TEA[e] | 4 | 2 | 200 |
| Comparative Example | CoAlPO-5 | 0.96Al:1.5P:0.8R:40H$_2$O | MDCHA[f] | 4 | 2 | 200 |
| Comparative Example | MnAlPO-5 | 0.96Al:1.5P:0.8R:40H$_2$O | TEA | 4 | 2.45 | 150 |
| Comparative Example | MnAlPO-5 | 0.96Al:1.5P:0.8R:40H$_2$O | MDCHA | 4 | 2 | 150 |
| Comparative Example | TiAlPO-5 | 0.96Al:1.5P:0.8R:40H$_2$O | TEA | 2 | 5 | 180 |
| Comparative Example | TiAlPO-5 | 0.96Al:1.5P:0.8R:50H$_2$O | MDCHA | 4 | 2 | 180 |
| Comparative Example | CoMnAlPO-5 | 0.96Al:1.5P:0.8R:40H2O | TEA | 6 | 3 | 170 |
| Comparative Example | CoMnAlPO-5 | 0.94Al:1P:0.75R:20H$_2$O | MDCHA | 6 | 2-24 | 180 |
| Comparative Example | CoMnAlPO-5 | 0.94Al:1.5P:0.8R:50H$_2$O | MDCHA | 12 | 2 | 180 |
| Comparative Example | CoMnAlPO-5 | 0.94Al:1.5P:0.8R:50H$_2$O | MDCHA | 18 | 2 | 180 |
| Catalyst Example 1 | CoTiAlPO-5 | 0.94Al:1.5P:0.8R:50H$_2$O | MDCHA | 6 | 2 | 170 |
| Catalyst Example 2 | CoTiAlPO-5 | 0.94Al:1.5P:0.8R:50H$_2$O | MDCHA | 12 | 2 | 180 |
| Catalyst Example 3 | CoTiAlPO-5 | 0.94Al:1.5P:0.8R:50H$_2$O | MDCHA | 18 | 2 | 180 |
| Catalyst Example 4 | MnTiAlPO-5 | 0.94Al:1.5P:0.8R:40H$_2$O | MDCHA | 6 | 2 | 180 |
| Catalyst Example 5 | MnTiAlPO-5 | 0.94Al:1.5P:0.8R:50H$_2$O | MDCHA | 12 | 2 | 200 |
| Catalyst Example 6 | MnTiAlPO-5 | 0.94Al:1.5P:0.8R:50H$_2$O | MDCHA | 18 | 2 | 200 |

[a]Structure directing agent,
[b]Total metal added to initial gel,
[c]Crystallization time,
[d]Crystallization temperature,
[e]triethylamine,
[f]N-methyldicyclohexylamine

TABLE 2

ICP analysis

| AlPO-5 | Atom % (gel) | | | Wt % from ICP | | | Wt %$_{(calc)}$ theory | | | Wt % difference | | | Atom %$_{(calc)}$ from ICP | | |
|---|---|---|---|---|---|---|---|---|---|---|---|---|---|---|---|
|  | Co | Mn | Ti | Co | Mn | Ti | Co | Mn | Ti | Co | Mn | Ti | Co | Mn | Ti |
| CoMn | 1 | 1 |  | 0.43 | 0.39 |  | 0.48 | 0.44 |  | 0.05 | 0.05 |  | 0.87 | 0.89 |  |
| CoMn | 3 | 3 |  | 1.48 | 1.32 |  | 1.42 | 1.33 |  | −0.1 | 0.01 |  | 2.98 | 2.99 |  |
| CoMn | 6 | 6 |  | 2.59 | 2.85 |  | 2.81 | 2.62 |  | 0.22 | −0.23 |  | 5.52 | 6.5 |  |
| CoMn | 9 | 9 |  | 3.75 | 3.46 |  | 4.16 | 3.88 |  | 0.41 | 0.42 |  | 8.07 | 9.15 |  |
| CoTi | 1 |  | 1 | 0.47 |  | 0.39 | 0.48 |  | 0.39 | 0.01 |  | 0 | 0.97 |  | 0.99 |

TABLE 2-continued

ICP analysis

| AlPO-5 | Atom % (gel) | | | Wt % from ICP | | | Wt %$_{(calc)}$ theory | | | Wt % difference | | | Atom %$_{(calc)}$ from ICP | | |
|---|---|---|---|---|---|---|---|---|---|---|---|---|---|---|---|
| | Co | Mn | Ti | Co | Mn | Ti | Co | Mn | Ti | Co | Mn | Ti | Co | Mn | Ti |
| CoTi | 3 | | 3 | 1.35 | | 1.29 | 1.43 | | 1.16 | 0.08 | | −0.1 | 2.83 | | 3.32 |
| CoTi | 6 | | 6 | 2.39 | | 2.24 | 2.83 | | 2.3 | 0.44 | | 0.06 | 5.08 | | 5.85 |
| CoTi | 9 | | 9 | 3.61 | | 3.1 | 4.19 | | 3.41 | 0.58 | | 0.31 | 7.76 | | 8.2 |
| MnTi | | 1 | 1 | | 0.41 | 0.39 | | 0.45 | 0.39 | | 0.04 | 0 | | 0.91 | 0.99 |
| MnTi | | 3 | 3 | | 1.73 | 1.32 | | 1.33 | 1.16 | | −0.4 | −0.2 | | 4.49 | 3.39 |
| MnTi | | 6 | 6 | | 2.08 | 2.48 | | 2.64 | 2.3 | | 0.56 | −0.2 | | 5.4 | 6.44 |
| MnTi | | 9 | 9 | | 3.17 | 3.43 | | 3.92 | 3.42 | | 0.75 | −0 | | 8.32 | 9 |

TABLE 3

ICP analysis

| MAlPO | Gel Composition | SDA$^a$ | Loading$^b$ (Atom %) | ICP loading (Wt %) | Time$^c$ (hours) | Temp$^d$ |
|---|---|---|---|---|---|---|
| CoAlPO-5 | 0.96Al:1.5P:0.8R:40H$_2$O | TEA$^e$ | 4 | 1.9 | 2 | 200 |
| CoAlPO-5 | 0.96Al:1.5P:0.8R:40H$_2$O | MDCHA$^f$ | 4 | 1.9 | 2 | 200 |
| MnAlPO-5 | 0.96Al:1.5P:0.8R:40H$_2$O | TEA | 4 | 1.8 | 2.45 | 150 |
| MnAlPO-5 | 0.96Al:1.5P:0.8R:40H$_2$O | MDCHA | 4 | 1.9 | 2 | 150 |
| TiAlPO-5 | 0.96Al:1.5P:0.8R:40H$_2$O | TEA | 2 | 2.0 | 5 | 180 |
| TiAlPO-5 | 0.96Al:1.5P:0.8R:50H$_2$O | MDCHA | 4 | 2.2 | 2 | 180 |
| CoMnAlPO-5 | 0.96Al:1.5P:0.8R:40H2O | TEA | 6 | 2.9 | 3 | 170 |
| CoMnAlPO-5 | 0.94Al:1P:0.75R:20H$_2$O | MDCHA | 6 | 2.8 | 2-24 | 180 |
| CoMnAlPO-5 | 0.94Al:1.5P:0.8R:50H$_2$O | MDCHA | 12 | 5.4 | 2 | 180 |
| CoMnAlPO-5 | 0.94Al:1.5P:0.8R:50H$_2$O | MDCHA | 18 | 7.2 | 2 | 180 |
| CoTiAlPO-5 | 0.94Al:1.5P:0.8R:50H$_2$O | MDCHA | 6 | 2.6 | 2 | 170 |
| CoTiAlPO-5 | 0.94Al:1.5P:0.8R:50H$_2$O | MDCHA | 12 | 4.6 | 2 | 180 |
| CoTiAlPO-5 | 0.94Al:1.5P:0.8R:50H$_2$O | MDCHA | 18 | 6.7 | 2 | 180 |
| MnTiAlPO-5 | 0.94Al:1.5P:0.8R:40H$_2$O | MDCHA | 6 | 3.0 | 2 | 180 |
| MnTiAlPO-5 | 0.94Al:1.5P:0.8R:50H$_2$O | MDCHA | 12 | 4.5 | 2 | 200 |
| MnTiAlPO-5 | 0.94Al:1.5P:0.8R:50H$_2$O | MDCHA | 18 | 6.6 | 2 | 200 |

Characterisation of all of the samples was carried out. Calcination was carried out using a Lenton thermal design tube furnace (serial no. 3/01/714). Powder x-ray diffraction of all the samples was carried out in Southampton on the Siemens D5000 diffractometer using Cu K$_{\alpha 1}$ radiation, $\lambda$=1.54056 Å. Further powder x-ray diffraction analysis was carried out at UOP LLC (Honeywell Group) using Scintag XDS 2000 with Cu tube. Diffuse Reflectance UV/Visible and in situ FT-IR were obtained in collaboration with Turin University, Italy. DR UV/Visible was obtained using a Perkin-Elmer Lambda 900 DR UV-Vis-NIR spectrometer with Win-Lab900 software while FT-IR was run on a Bruker IFS88 with 4 cm$^{-1}$ resolution. For these tests, the sample was put under vacuum (5×10$^{-4}$ mbar) before heating up slowly to 550° C. The vacuum was removed and oxygen was added (130 mbar) overnight as preparation for DR UV/Visible or FT-IR analysis. Ammonia gas was added stepwise, building up from 2 mbar to 50 mbar and analysis by FT-IR was carried out at each step. Scanning electron microscopy was carried out using a JSM5910 microscope with carbon coating during sample preparation. Basic results of EXAFS/XANES were carried out in Grenoble in collaboration with Turin University.

Catalysis Procedures and Analysis

Catalysis was carried out in a high pressure, in a mixture of PEEK and PTFE lined 0.1 liter Parr 4590 reactor and 4843 Parr controller while catalytic results were obtained using a Varian Star 3400CX gas chromatograph with flame ionization detector (FID). The method used an initial column temperature of 80° C., hold time 7 minutes, final column temperature 220° C. with a 10 minute hold time and a 3 degrees per minute temperature rise.

Two columns were used—column 1 used HP1 cross linked methylsiloxane (30m×0.32 mm×1 µm film thickness) and was used for the ammoximation reactions. Column 2 used HP-Innowax crosslinked polyethylene glycol (30m×0.53 mm×1 µm film thickness) and was used for the oxidation of cyclohexane and cyclohexanol. In each case the injector was set to 220° C. with detector at 300° C.

Figure 2:
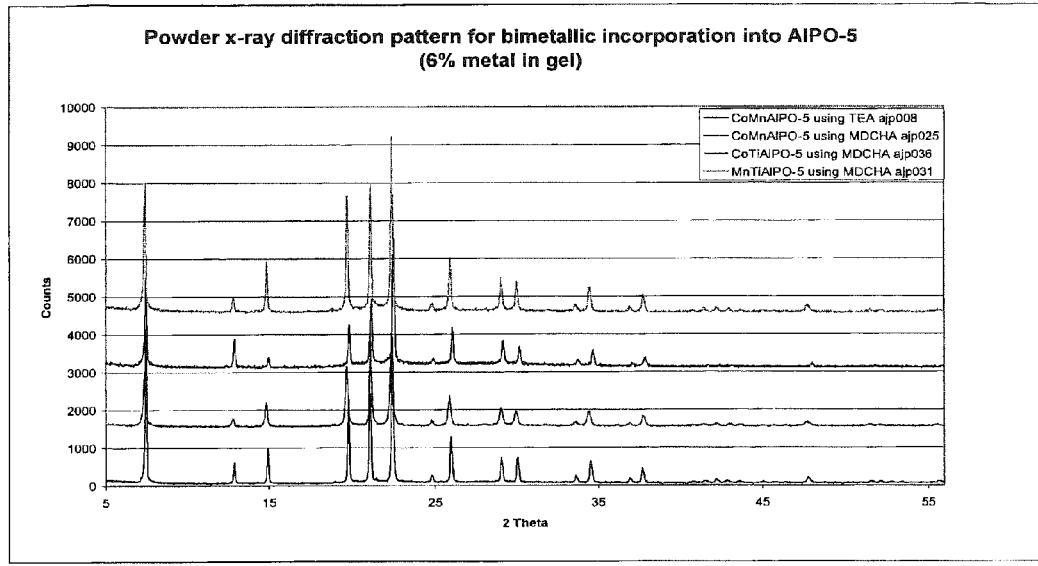
FIGS. 2 and 3 show X-Ray Diffraction Patterns of two metals incorporated into AlPO-5
Figure 3:
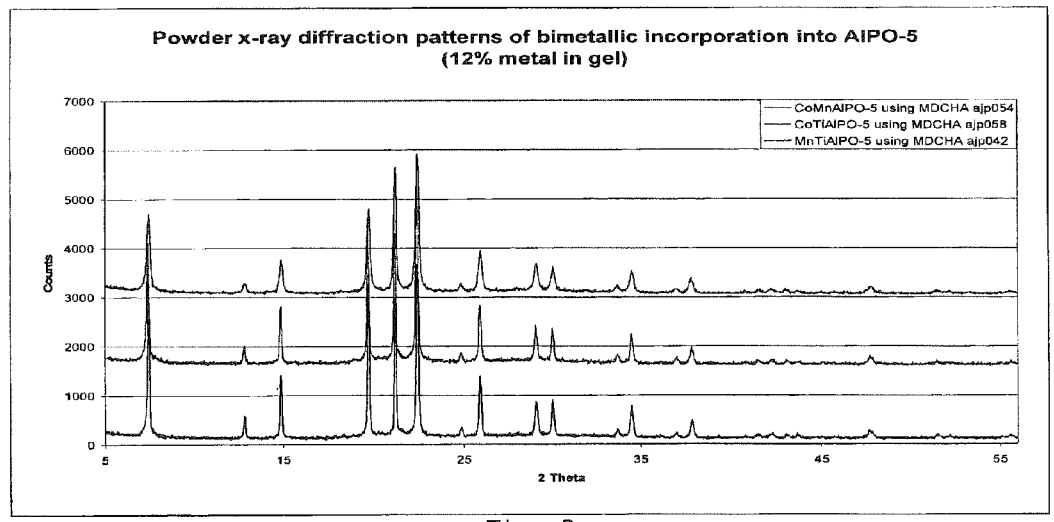

All of the samples listed in Table 1 were synthesized and tested using powder x-ray diffraction. Some of these diffraction patterns are shown below in FIGS. 2 and 3. CelRef was used to analyse these spectra and to assign hkl values to the peaks.

Figures 4, 5:
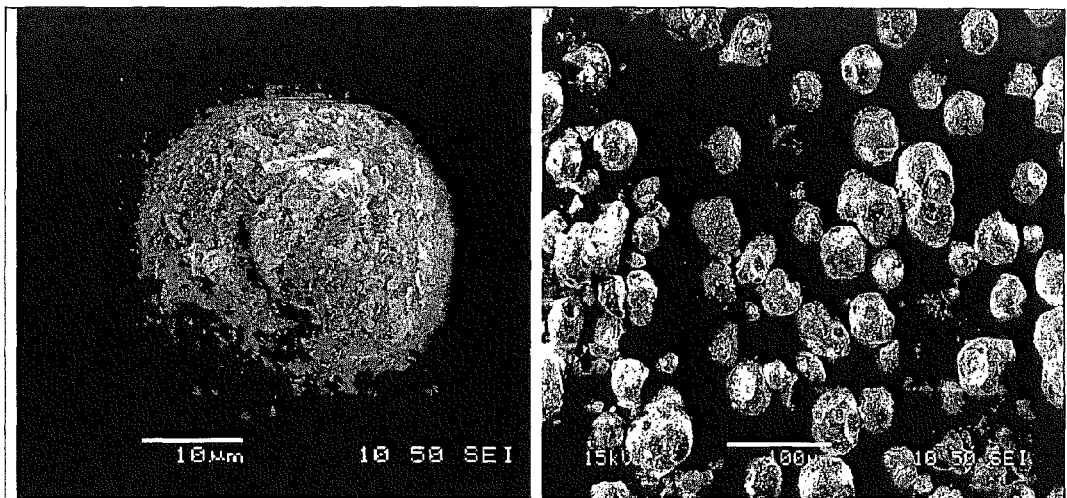
FIG. 4 shows a scanning electron microscopy image of CoMnAlPO-5
FIG. 5 shows a scanning electron microscopy image of CoTiAlPO-5
Figure 6:
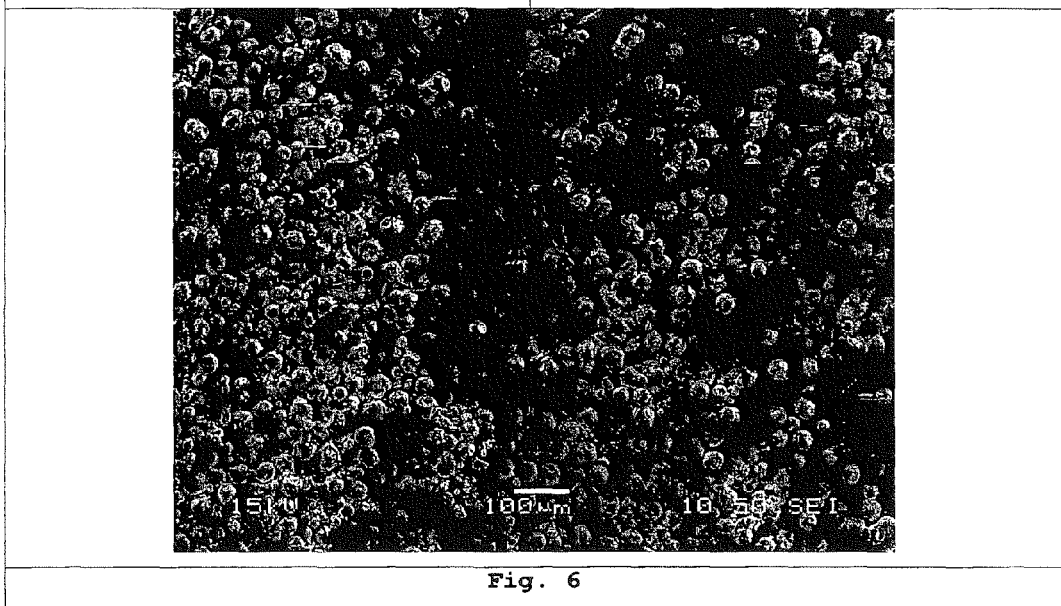
FIG. 6 shows a scanning electron microscopy image of MnTiAlPO-5

Scanning electron microscopy (SEM) was used to gain a more detailed analysis of the samples synthesized. Reports by Hsu and Balkus have reported SEM analysis of AFI frameworks showing spherical particles similar to those seen in FIGS. 4 to 6. The samples they report are of pure AlPO-5 while the SEM analysis of CoTiAlPO-5, CoMnAlPO-5 and MnTiAlPO-5 reported here are in good agreement and show particles with similar morphology. The three images shown in FIGS. 4 to 6, give examples of high, medium and low magnification images taken for each sample and are indicative of the AlPO-5 framework. In addition, the images shown below (and a number of other images collected) also show a consistent particle size and shape across the whole sample, with no indication of other products (eg $TiO_2$). A measurement of the particle sizes was taken and tabulated in Table 4, these vary significantly from sample to sample, several reports have shown AFI particles to range from 10-60 μm. The variations seen here are likely to be due to the differing synthesis conditions or the metal incorporated.

TABLE 4

Particle sizes obtained by SEM

| Calcined structure | Average particle size |
|---|---|
| CoMnAlPO-5 | 40 μm |
| CoTiAlPO-5 | 33 μm |
| MnTiAlPO-5 | 25 μm |

Ammoximation Gel Composition Data
Listed Below is the Ammoximation Gel Composition Data

| | |
|---|---|
| CoMnAlPO-5 | 0.94Al:1.5P:0.03Co:0.03Mn:0.8MDCHA:50H2O |
| CoTiAlPO-5 | 0.94Al:1.5P:0.03Co:0.03Ti:0.8MDCHA:50H2O |
| MnTiAlPO-5 | 0.94Al:1.5P:0.03Mn:0.03Ti:0.8MDCHA:50H2O |
| FeTiAlPO-5 | 0.94Al:1.5P:0.03Fe:0.03Ti:0.8MDCHA:50H2O |
| CrTiAlPO-5 | 0.94Al:1.5P:0.03Cr:0.03Ti:0.8MDCHA:50H2O |
| CuTiAlPO-5 | 0.94Al:1.5P:0.03Cu:0.03Ti:0.8MDCHA:50H2O |
| VTiAlPO-5 | 0.94Al:1.5P:0.03V:0.03Ti:0.8MDCHA:50H2O |
| RuTiAlPO-5 | 0.94Al:1.5P:0.03Ru:0.03Ti:0.8MDCHA:50H2O |

Ammoximation of Cyclohexanone

The catalyst (1 g) was added to the reactor vessel with 10 g (0.101 mol) cyclohexanone before being sealed and purged with nitrogen at 30 bar for 20 minutes. The pressure was released and 23.8 g (0.204 mol) of ammonium hydroxide (30% in water) was added by syringe before 30 bar of air was added. The reaction vessel was heated to 60° C. whilst stirring at 830 rpm, samples were removed at 20 minute intervals. The samples were centrifuged before 0.2 μl was injected into the gas chromatograph.

Catalytic Results

Catalytic tests were run on the calcined samples showing the ammoximation of cyclohexanone. The results of these are shown in table 5 below.

Table 5 Ammoximation of cyclohexanone using air and ammonia

TABLE 5

Aminoximation of cyclohexanone

| Catalyst (loading) | Substrate (mole) | Oxidant | Pressure (MPa) | Mole ratio Ketone:$NH_3$ | Solvent | Temp (K) | Time (mins) | Conv (mol %) | Oxime Selectivity (mol %) |
|---|---|---|---|---|---|---|---|---|---|
| CoMnAlPO-5 (5.44 wt %) (comparative Example) | cyclohexanone (0.1019) | Air | 3 | 1:2 | — | 333 | 20 | 32.4 | 93.0 |
| | | | | | | | 40 | 45.0 | 90 |
| | | | | | | | 60 | 55.9 | 86.9 |
| | | | | | | | 80 | 58.8 | 81.5 |
| | | | | | | | 100 | 69.0 | 79.5 |
| CoTiAlPO-5 (4.63 wt %) | cyclohexanone (0.1019) | Air | 3 | 1:2 | — | 333 | 20 | 49.6 | 90.5 |
| | | | | | | | 40 | 57.6 | 89.8 |
| | | | | | | | 60 | 67.3 | 85.4 |
| | | | | | | | 80 | 69.0 | 85.1 |
| | | | | | | | 100 | 72.6 | 85.0 |
| MnTiAlPO-5 (4.56 wt %) | cyclohexanone (0.1019) | Air | 3 | 1:2 | — | 333 | 20 | 46.0 | 82.7 |
| | | | | | | | 40 | 63.1 | 87.6 |
| | | | | | | | 60 | 68.9 | 85.1 |
| | | | | | | | 80 | 68.1 | 78.8 |
| | | | | | | | 100 | 67.3 | 76.5 |

[1]TON = [(mol$_{substr}$) (mol$_{metal}$)$^{-1}$ where mol$_{substr}$ = mols of cyclohexanone converted Cyclohexanone was converted to cyclohexanone oxime using ammonia and air in the Parr pressure reactor. The initial results show a good conversion and selectivity for the oxime with CoMnAlPO-5 and CoTiAlPO-5. CoTiAlPO-5 gave the best selectivity, greater than 85% throughout the reaction while also giving the best turn over (100-150).

The invention claimed is:

1. A redox ammoximation process comprising reacting a $C_6$-$C_{12}$ cyclic ketone with ammonia and oxygen in the presence of a catalyst to form an oxime, wherein:
   the catalyst is an aluminophosphate based redox catalyst having the formula (I)

$M^1M^2AlPO$-5            (I)

wherein $M^1$ is at least one selected from Co(III), Mn(III), Fe(III), Cu(III), V(V), and Ru(III) having redox catalytic capability;
   $M^2$ is at least one selected from Ge(IV), Sn(IV), Ti(IV), and Re(IV); and
   a proportion of the phosphorous atoms in the $M^1M^2AlPO$-5 type structure are replaced by $M^2$ atoms.

2. A process according to claim 1 when $M^2$ is Ti (IV).

3. A process according to claim 2 wherein the catalyst is selected from $Co^{III}Ti^{IV}$ AlPO-5, $Mn^{III}Ti^{IV}$ Alpo-5, $Fe^{III}Ti^{IV}$ AlPO-5, $Cu^{III}Ti^{IV}$ AlPO-5, $V^VTi^{IV}$ AlPO-5, and $Ru^{III}Ti^{IV}$ AlPO-5.

4. A process according to claim 3 wherein the catalyst is selected from $Co^{III}Ti^{IV}$ AlPO-5, $Mn^{III}Ti^{IV}$ AlPO-5 and $Fe^{III}Ti^{IV}$ AlPO-5.

5. A process according to claim 1 wherein the $M^1$ is selected from Co(III), Mn(III) and Fe (III).

6. A process according to claim 1 wherein the ammonia is in the form of aqueous ammonium hydroxide.

7. A process according to claim 1 which is carried out at a temperature of from 40 to 200° C.

8. A process according to claim 7 which is carried out at a temperature of from 50 to 90° C.

9. A process according to claim 1 which is carried out at a pressure of from 0.5 MPa [5 bar] to 10 MPa [100 bar].

10. A process according to claim 1 wherein the $C_6$-$C_{12}$ ketone is cyclohexanone and the oxime is cyclohexanone-oxime.

11. A process of forming an ϵ-caprolactam comprising reacting cyclohexanone with ammonia and oxygen in the presence of a catalyst to form an cyclohexanone oxime, wherein:

the catalyst is an aluminophosphate based redox catalyst having the formula (I)

$M^1M^2AlPO-5$ (I)

wherein $M^1$ is at least one selected from Co(III), Mn(III), Fe(III), Cu(III), V(V), and Ru(III) having redox catalytic capability;

$M^2$ is at least one selected from Ge(IV), Sn(IV), Ti(IV), and Re(IV); and a proportion of the phosphorous atoms in the $M^1M^2AlPO-5$ type structure are replaced by $M^2$ atoms; and converting the oxime to an ϵ-caprolactam.

12. An aluminophosphate based redox catalyst having the formula (I)

$M^1M^2AlPO-5$ (I)

in which $M^1$ is at least one selected from Co(III), Mn(III), Fe(III), Cu(III), V(V), and Ru(III) having redox catalytic capability;

$M^2$ is at least one selected from Ge(IV), Sn(IV), Ti(IV), and Re(IV); and a proportion of the phosphorous atoms in the $M^1M^2AlPO-5$ type structure are replaced by $M^2$ atoms.

13. A process according to claim 1 wherein 2 to 18 wt % by weight of the phosphorous atoms in the $M^1M^2AlPO-5$ type structure are replaced by $M^2$ atoms.

14. A catalyst according to claim 12 wherein 2 to 18 wt % by weight of the phosphorous atoms in the $M^1M^2AlPO-5$ type structure are replaced by $M^2$ atoms.

* * * * *